US009597528B2

(12) United States Patent
Schomacker et al.

(10) Patent No.: US 9,597,528 B2
(45) Date of Patent: Mar. 21, 2017

(54) APPLICATOR

(71) Applicant: Candela Corporation, Wayland, MA (US)

(72) Inventors: Kevin Schomacker, Maynard, MA (US); Xiaoming Shang, Lexington, MA (US); Herbert R. Otterson, Needham, MA (US); Antonio Paulino, Watertown, MA (US)

(73) Assignee: Candela Corporation, Wayland, MA (US)

( * ) Notice: Subject to any disclaimer, the term of this patent is extended or adjusted under 35 U.S.C. 154(b) by 98 days.

(21) Appl. No.: 14/484,302

(22) Filed: Sep. 12, 2014

(65) Prior Publication Data

US 2016/0074672 A1 Mar. 17, 2016

(51) Int. Cl.
*A61N 5/06* (2006.01)
*A61F 7/00* (2006.01)
(Continued)

(52) U.S. Cl.
CPC ............ *A61N 5/0625* (2013.01); *A61B 18/14* (2013.01); *A61B 18/201* (2013.01); *A61B 18/203* (2013.01); *A61F 7/007* (2013.01); *A61N 5/0616* (2013.01); *A61B 2018/00029* (2013.01); *A61B 2018/00047* (2013.01); *A61B 2018/00458* (2013.01); *A61B 2018/00476* (2013.01); *A61B 2018/00815* (2013.01); *A61B 2018/00821* (2013.01); *A61B 2018/00994* (2013.01); *A61B 2018/1497* (2013.01); *A61B 2018/2025* (2013.01); *A61B 2018/2035* (2013.01); *A61B 2018/2266* (2013.01); *A61F 2007/0063* (2013.01); *A61N 2005/007* (2013.01); *A61N 2005/067* (2013.01); *A61N 2005/0644* (2013.01); *A61N 2005/0651* (2013.01);
(Continued)

(58) Field of Classification Search
CPC .......... A61N 5/0625; A61N 2005/0666; A61B 18/22
USPC ......................... 606/2, 9–11, 13, 17; 607/89
See application file for complete search history.

(56) References Cited

U.S. PATENT DOCUMENTS 6,682,524 B1 * 1/2004 Elbrecht .............. A61B 18/203
606/13
6,702,808 B1 3/2004 Kreindel
(Continued)

FOREIGN PATENT DOCUMENTS

WO 2011037122 A1 3/2011
WO 2013079785 A1 2/2013

OTHER PUBLICATIONS

Wikipedia, Lens (optics), Published Jan. 19, 2013, http://en.wikipedia.org/wiki/Lens_(optics).*
(Continued)

*Primary Examiner* — Christopher A Flory
*Assistant Examiner* — Johnathan Kuo
(74) *Attorney, Agent, or Firm* — Manelli Selter PLLC; Edward J. Stemberger (57) ABSTRACT

Disclosed is an applicator or handpiece configured to apply treatment energy to a segment of skin located in a tissue or skin treatment plane. The treatment energy could be RF energy, applied by a pair of bipolar RF electrodes or optical energy. The applicator includes an optical system configured to form a rectangular spot and homogenize the optical energy distribution.

23 Claims, 5 Drawing Sheets

(51) Int. Cl.
    *A61B 18/20*     (2006.01)
    *A61B 18/14*     (2006.01)
    *A61N 5/067*     (2006.01)
    *A61B 18/00*     (2006.01)
    *A61B 18/22*     (2006.01)
    *A61N 5/00*     (2006.01)

(52) U.S. Cl.
    CPC ........... *A61N 2005/0655* (2013.01); *A61N 2005/0666* (2013.01)

(56) References Cited

U.S. PATENT DOCUMENTS

| | | |
|---|---|---|
| 2005/0215987 A1 | 9/2005 | Slatkine |
| 2006/0116669 A1* | 6/2006 | Dolleris ............... A61B 18/203 606/17 |
| 2008/0287930 A1 | 11/2008 | Rapoport |
| 2010/0049177 A1* | 2/2010 | Boone, III ........... A61H 9/0057 606/9 |
| 2011/0166559 A1* | 7/2011 | Eckhouse ............. A45D 26/00 606/9 |
| 2013/0030506 A1 | 1/2013 | Bartolone et al. |
| 2013/0190738 A1 | 7/2013 | Lukac et al. |

OTHER PUBLICATIONS

International Search Report and Written Opinion in PCT/US2015/048500 dated Jan. 19, 2016.

* cited by examiner

APPLICATOR

TECHNOLOGY FIELD

The present applicator relates to the field of cosmetic treatment and in particular to cosmetic skin treatment.

BACKGROUND

Cosmetic skin treatment is typically performed by application of heat to a segment of skin to be treated. The heat could be generated by application of Radio Frequency (RF), Intense Pulse Light (IPL), laser radiation, ultrasound or a combination of the above energies. Almost all of the skin treatment energies are applied to the skin by a tool termed applicator or handpiece. For example, applicators configured to apply to the skin a combination of RF and IPL or laser light systems such as the one disclosed in U.S. Pat. No. 6,702,808 to the same assignee and other similar systems. The particular applicator includes a long rectangular light guide placed between two bipolar RF electrodes. Concurrent application to the skin of RF energy and light energy allows addressing of skin layers located at different depth at the same treatment. Heating of the tissue via the different energies is additive, sometimes the sum being greater than the parts. The different energies may enter the skin at different locations. The energies applied to the treated skin segment and in particular light energy, are not distributed uniform across the treated skin or tissue segment. Typically the light energy decreases exponentially as the light passes deeper into tissue while in skin, the RF energy decreases laterally as you move away from the electrode. The combination of the two helps to better homogenize tissue heating. When the applicator is moved across the skin with a single energy source, some of the areas of the skin segment could be over treated and even burned and some of the areas could be undertreated. Because of these differences multiple sources allows reduction of each of the energies and diminishes the danger of skin burning.

The adverse effects caused by application of large amount of heat, particularly light, to the treated skin or tissue segment could be somehow mitigated by concurrent gradient cooling of the treated tissue. Cooling of the tissue segment located in a tissue or skin treatment plane is usually performed by cooling an applicator element being in contact with the skin treatment plane. Methods of applying a cooled fluid spray directly to the tissue or skin treatment plane are also known.

U.S. Pat. Nos. 6,383,176, 6,485,484, 6,666,856, 7,465,307, and 8,474,463 disclose different skin treatment applicators.

SUMMARY

Disclosed is an applicator or handpiece configured to apply treatment energy to a segment of skin located in a tissue or skin treatment plane. The treatment energy could be RF energy, applied by a pair of bipolar RF electrodes or optical energy, or a combination of RF and optical energies. The optical energy wavelength could be selected from a number of different optical energy sources as it could be desired by a particular skin treatment.

The applicator or handpiece include a support structure with a frame configured to hold a transparent window. The transparent window defines the tissue or skin treatment plane. The support structure is angled with respect to axis of symmetry of the applicator at an angle of 10 to 30 degrees. The angled with respect to the axis of symmetry support structure gives to operator or caregiver a better view of the tissue treatment plane or area compared to that of an applicator designed to be applied perpendicular to the treatment plane.

In one example, the applicator includes an optical system configured to receive a beam of optical energy from a source of optical energy and convey or funnel it to the tissue treatment plane. The frame with or without the transparent window defines the tissue treatment plane. The beam of optical energy could be conducted from the source of optical energy to the applicator by a fiber optics guide or with the help of an articulated arm. Although the fiber optics guide homogenizes optical energy distribution across the beam of optical energy, the optical system could use a tapered light pipe homogenizer and a pair of lenses. When an articulated arm is used to conduct the optical energy from the source of optical energy to the applicator, the optical system includes a tapered light pipe homogenizing rod configured to homogenize the cross section of the beam of optical energy and a pair of lenses. The taper can help improve homogenization plus allow smaller diameter optics downstream.

The output facet of the tapered light pipe homogenizing rod is configured to shape the beam of optical energy at the tissue treatment plane. The optical system is configured to receive the homogenized beam of optical energy from the tapered light pipe homogenizing rod and image the beam shaping output facet of the light pipe homogenizing rod onto a treated skin or tissue plane. Although not inclusive, examples of the output facet could include circular, oval, rectangular, and trapezoidal. In some examples, the image of the output facet of the light pipe homogenizing rod at the tissue treatment plane has a circular or oval shape. In one example, the tapered light pipe homogenizing rod is a tapered trapezoidal prism. The image of the beam shaping output facet of the tapered trapezoidal prism at the tissue treatment plane has a square or rectangular shape.

One important distinction of the tapered light pipe homogenizing rod over the known art is that the tapered light pipe homogenizing rod is not placed between the electrodes or makes contact with the tissue treatment plane but is placed proximal to and spaced from the tissue treatment plane. This change improves the user's view of the tissue treatment plane as there is no longer a need to look through the light pipe to see the treatment field, reducing distortion.

To correct for the circular to oval or square/rectangular to trapezoidal shape distortion caused by the angled support structure, the output facet of the tapered light pipe is selected to be oval or trapezoidal, respectively.

To further correct for a distortion of the intensity field at the tissue treatment plane that could be caused by the angled support structure, the pair of lenses is placed at an angle of 6 to 10 degrees to axis of the applicator. A smaller degree tilting of the lenses is used in a 10 degree off-axis applicator while a larger degree tilt used in the 30 degree off-axis applicator. The tilt depends on the specific lenses used and whether or not astigmatic lenses are used to reduce the distortion at the treatment plane.

In one example, the angled support structure of the applicator is configured to support in addition to the transparent window a pair or more than a pair of the bi-polar RF electrodes. The tissue treatment plane could be located between the pair or pairs of the bipolar RF electrodes.

In another example, the applicator includes an optical system configured to receive a beam of optical energy from a source of optical energy and convey it to the tissue located in the tissue treatment plane. The tissue treatment plane is located between the pair of the bipolar RF electrodes. The optical system includes a trapezoidal prism or a tapered trapezoidal prism configured to homogenize the cross section of the beam of optical energy and a pair of lenses. The optical system is configured to receive the homogenized beam of optical energy from the trapezoidal prism and image trapezoidal output facet of the trapezoidal prism to a treated skin or tissue plane located between the pair of bipolar RF electrodes. The support structure is angled between 10 to 30 degrees with respect to the tissue treatment plane. The image of the output of the trapezoidal prism facet at the tissue treatment plane has a rectangular shape.

To correct for distortion in the intensity field at the treatment plane that could be caused by the angled support structure, the pair of lenses is placed at an angle of 6 to 10 degrees to axis of the applicator. Table 1 provides examples of the support structure angles and tilt of the optics that facilitates formation of a round, oval, square or rectangular image shape spot.

TABLE 1

| Image Shape | Support Structure | Output Facet | Tilted Optics |
|---|---|---|---|
| Circular | 0 degrees | Circular | 0 degrees |
|  | 10-30 degrees | Oval | 6 to 10 degrees |
| Oval | 0 degrees | Oval | 0 degrees |
|  | 10-30 degrees | Oval | 6 to 10 degrees |
| Square | 0 degrees | Square | 0 degrees |
|  | 10-30 degrees | Trapezoidal | 6 to 10 degrees |
| Rectangular | 0 degrees | Rectangular | 0 degrees |
|  | 10-30 degrees | Trapezoidal | 6 to 10 degrees |

The skin treatment could be performed by application of RF energy only, optical energy only or a combination of RF energy and optical energy. Each of the applicators could include a cooling arrangement configured to cool the tissue or skin treatment plane to which the treatment energy is applied. The cooling arrangement could cool the transparent window, which in course of treatment is in contact with the tissue or skin treatment plane and cools it. In another example, the tissue or skin treatment plane could be cooled by applying to it a cryogenic spray.

The applicator or handpiece significantly improve observation of the tissue or skin treatment plane and facilitate the work of the operator or caregiver, providing unobstructed view of the tissue or skin treatment plane immediately prior to, during, and after the delivery of a treatment pulse without the need of removing the application from the field. The angled support structure and the placement of the homogenizing light pipe more proximal to the tissue treatment plan helps to improve the user's view of the treatment field before, during and after delivering the treatment energy.

GLOSSARY

Tapered light homogenizing pipe and tapered trapezoidal prism or tapered light homogenizing trapezoidal prism—as used in the current disclosure means a light pipe homogenizing rod that utilizes total internal reflection to homogenize non-uniform optical sources energy distribution regardless of their spectral characteristics. Although the taper is preferred and offers additional characteristics, the taper is not critical to this application. Such optical elements are available from a number of suppliers, for example from Edmund Scientific, Inc. In the above example the taper is along the axial axis. Axial-lateral tapered light pipe homogenizing rods or prisms having tapers along the axial and lateral axes are also subject to this disclosure and can be obtained from skilled optics shops by modifying axially tapered rods or prisms. In addition to homogenizing energy distribution across the beam of optical energy the taper of the homogenizing rods could be used to shape the image of the tapered output facet of the homogenizing rod.

DESCRIPTION

Concurrent application to the tissue or skin located in the treatment plane of RF energy and light energy allows addressing of skin or tissue layers located at different depth at one treatment. It allows reduction of each of the energies and diminishes the danger of skin burning. The RF electrodes obstruct the field of view of the operator and make it difficult to observe the treated skin segment. The light energy is conducted to the tissue or skin treatment plane by internal reflections from the walls of the light guide and do not allow visual tissue or skin treatment plane monitoring. Observation or visualization during cosmetic skin treatment procedures is important to the operator and/or caregiver. It supports real time observation of visible changes in the treated vessels or other targets in skin and facilitates the accurate placement of the applicator from one application of the skin treatment energy, to the next application of skin treatment energy.

Many cosmetic light based treatments are performed with a round light or optical energy spot. Many of the cases the treatment light intensity is not homogenously distributed across the light spot. To cover neighboring areas to the spot skin surface, the spot is stepped or continuously moved in a desired direction. The round shape of the treatment optical energy spot forces certain amount of overlap if complete skin coverage is desired. Without overlap some untreated skin areas will result. This may lead to over treatment in the overlapped areas or under treatment in the untreated areas. Having a square or rectangular light spot could bring better treatment coverage and end results.

Cooling of the tissue located in a tissue treatment plane is usually performed by cooling an applicator element being in contact with the tissue located in the treatment plane. Absence of effective cooling of the epidermis while heating the dermis and deeper skin layers during the course of optical (laser) energy treatments can cause undesired pain to the treated subject and potentially undesired skin injury. Traditional modes—topical applications, forced cold air, and contact cooling—cool imperfectly, are often too long and cool too deeply. Such methods force additional laser energy to be used to reheat the dermis. Therefore, either treatment fluence needs to be raised or the therapeutic value is diminished.

The assignees of the current disclosure have experimentally proved that direct cryogen liquid drops of cryogen spraying on the tissue treatment plane is one of the most effective user independent tissue cooling methods.

Figure 1:
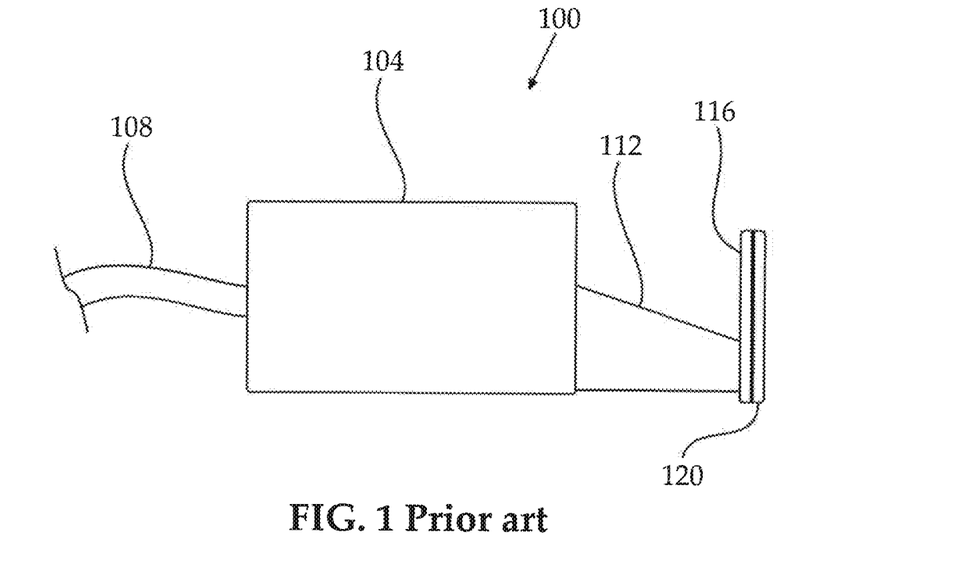
FIG. 1 is a simplified illustration of an existing applicator.

Reference is made to FIG. 1, which is a simplified illustration of an existing applicator or handpiece according to an example. This illustration is intended to depict a skin contact cooling applicator having features that are different compared to a cryogen spray application. Applicator 100 includes a convenient to handle housing 104 connected by a cable 108 to a power supply (not shown) and to a source of optical energy that could be incorporated in the power supply packaging. The source of optical energy could be a suitable laser or an IPL source. The beam of light energy is conducted from the source of the optical energy to the tissue or skin treatment plane by a fiber optics guide or with the help of an articulated arm and is projected onto the tissue or skin treatment plane as a round spot. A pair of support columns 112 or a single support column holding a frame 116 into which a transparent window 120 is inserted. Window 120 is usually made of sapphire or quartz. Columns 112 and frame 116 are usually made of metal or other good heat conducting material and are connected to a cooling device (not shown). The frame is in thermal communication with window 120, which is in contact with the tissue or skin and cools the tissue or skin located at the treatment plane 124.

Figure 2:
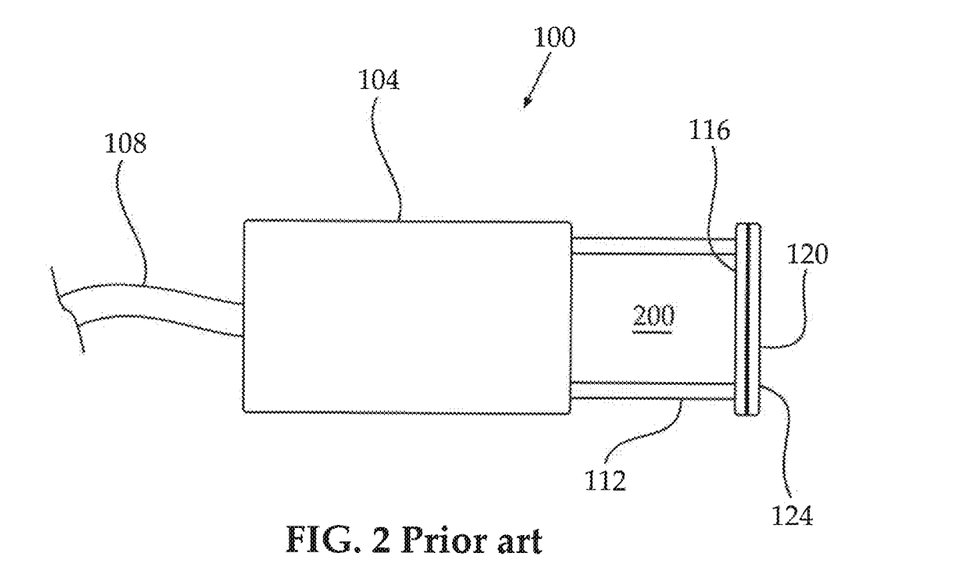
FIG. 2 is a top view of the applicator of FIG. 1.

FIG. 2 is a pseudo top view of the applicator of FIG. 1. It illustrates opening 200 through which the operator or caregiver using the applicator can observe the tissue or skin treatment plane. In course of skin treatment applicator 100 is oriented perpendicular to the tissue or skin treatment plane and still partially obstructs the field of view of the operator. This makes applicator movement over the skin inconvenient.

Figure 3:
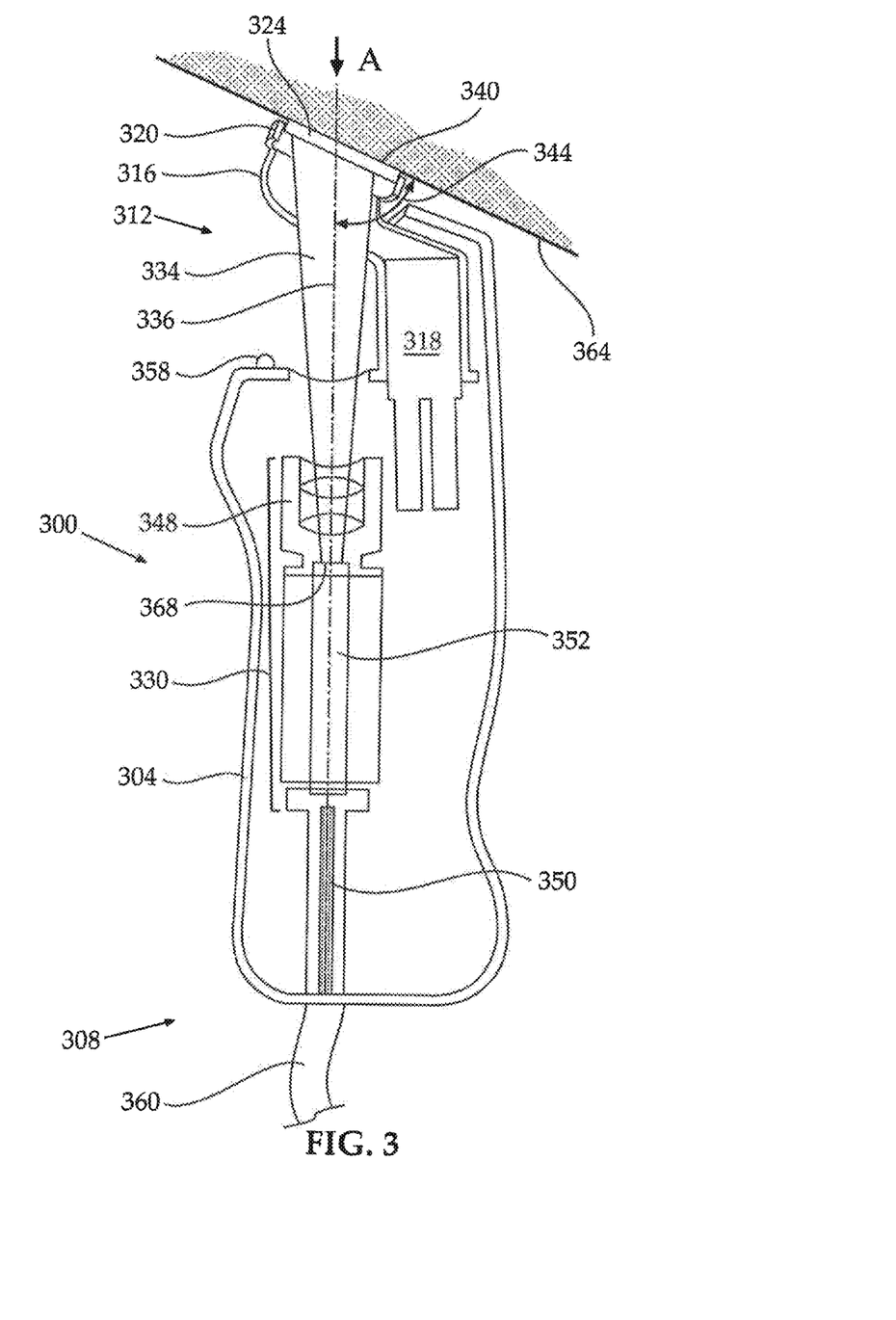
FIG. 3 is a simplified illustration of an applicator according to an example.

FIG. 3 is a simplified illustration of an applicator according to an example. Applicator or handpiece 300 includes a housing 304 with a proximal 308 and a distal 312 end. A support structure 316 including two support columns is terminated by a frame 320 that extends from distal end 312. Support structure 316 is angled to applicator 300 axis of symmetry 336 or off normal relative to axis of symmetry 336 of applicator 300 and improve line of sight to the skin treatment plane or skin area to be treated 340. The compliment of angle 344 at which support structure 316 is angled could be 10 to 30 degrees and usually the angle could be about 15 degrees.

Frame 320 holds an easy removable and replaceable window 324. Frame 320 could have a round, elliptical or a rectangular shape. Support structure 316 and frame 320 are made of metal or other material supporting good heat or cold conducting properties and are in thermal communication with a thermoelectric cooler 318. Replaceable window 324 could be made of sapphire or quartz.

In one example, removable window 324 could be removed to facilitate unobstructed access to the tissue or skin treatment plane. A cryogen spray-equipped cooling system could be configured to deliver the spray or liquid drops of cryogen onto surface to the tissue or skin treatment plane. The cryogen cooling could be implemented using the DCD cryogen cooling system commercially available from the assignee of the current application.

Applicator 300 further includes an optical system 330 configured to receive a beam of optical energy 334 from a source of optical energy (not shown) and to direct the beam of optical energy 334 to irradiate the skin or tissue treatment plane 340 defined by frame 320 and being in contact with replaceable window 324 in the tissue or skin treatment plane 340. Beam of optical energy 334 could be conducted from a source of optical energy (not shown) for example, by a fiber optics guide 350.

Optical system of applicator 300 could include a light pipe tapered homogenizing rod 352 configured to receive beam of optical energy 334 from the source of optical energy and funnel the beam of optical energy 334 towards an output facet 368 that is oval or circular in cross-section. The output facet 368 of the tapered homogenizing rod 352 has an oval shape in order to form a circular beam at the tissue treatment plane 340 when the applicator's axis of symmetry 336 is tilted relative to the tissue treatment plane 340. The output facet 368 of the homogenizing rod 352 has an oval or circular shape in order to form an oval or circular beam at the tissue treatment plane 340 when the applicator's axis of symmetry 336 is not tilted relative to the tissue treatment plane 340. Simple geometric formulas can be used to relate the ratio of the major and minor axis of the oval/ellipse to the tilt angle in the optical axis. The light pipe homogenizing rod can be tapered to have a larger input facet (proximal to the fiber end) than the output facet to simplify coupling of the output of fiber optics guide. A smaller distal end or output facet preserves the homogenization of the beam of optical energy 334 and allows imaging or the output facet to the tissue treatment plane 340 without having to resort to large diameter optics. Tapered homogenizing rods also allow the use of shorter rods to homogenize the light energy at the treatment plane 340.

The light pipe homogenizing rod 352 could be such as a multi-facet tapered prism or a hollow light guide with a reflective coating deposited on the inner surfaces of the light guide.

Figure 4:
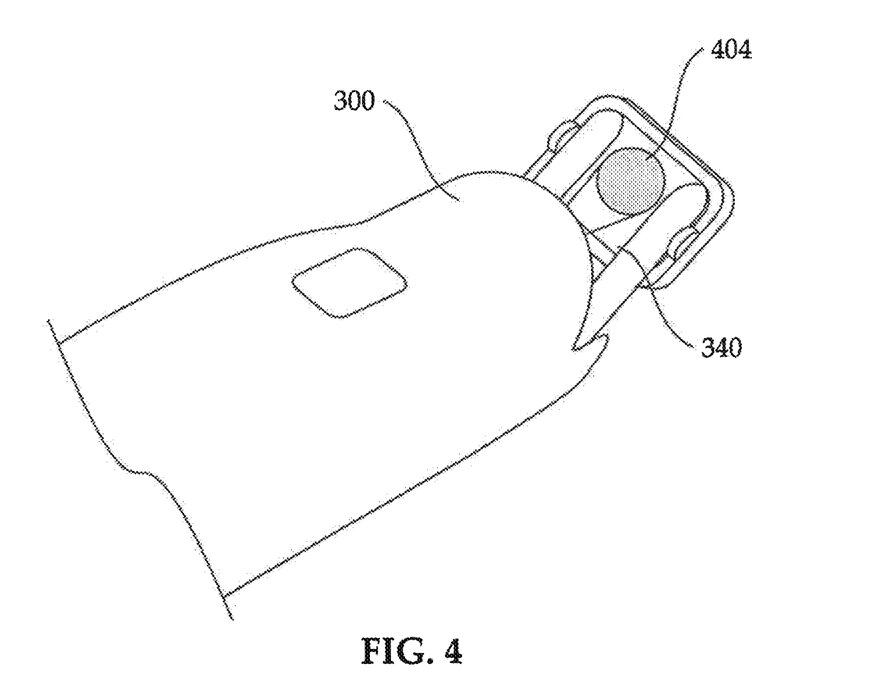
FIG. 4 is an example of an image or round spot formed by optical system of the applicator of FIG. 3 in the tissue or skin treatment plane.

Optical system 330 of applicator 300 could further include a pair of lenses 348 configured to receive a homogenized beam of optical energy 334 and image the output facet 376 of homogenizing rod 352 to a treated skin or tissue area 340 defined by frame 320 and being in contact with replaceable window 324 in the tissue or skin treatment plane 340. The image 404 (FIG. 4) of output facet 368 of homogenizing rod 352 could have an oval shape or a shape of a multi-faceted polygon approximating an oval shape. To correct for distortion of the intensity field that could be caused by the angled support structure, the pair of lenses is placed at an angle of 6 to 10 degrees to axis of the applicator. FIG. 4 illustrates a corrected round or circular shape image 404 of oval output facet 368 of light pipe homogenizing rod 352. Distribution of optical energy across image 404 of output facet 368 is homogenized.

Figure 3A:
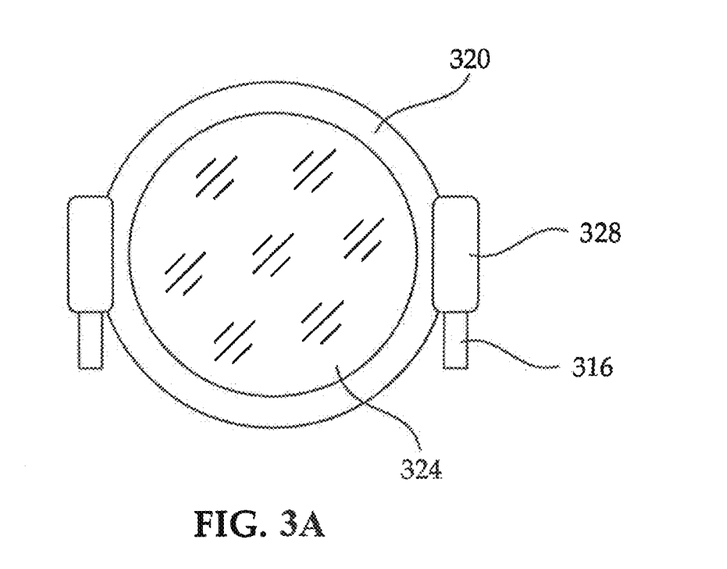
FIG. 3A is a view taken along the arrow A in FIG. 3.

In one example illustrated in FIG. 3A a pair of bipolar RF electrodes 328 could be mounted on support structure 316 located on distal end 312 of housing 304. Electrodes 328 could be configured to apply RF energy to tissue 364 located in tissue treatment plane 340. Electrodes 328 (FIG. 3A) could be mounted on frame 320 or mounted directly to the transparent window. Optical system 330 could be configured to receive a homogenized beam of optical energy 334 from light pipe homogenizing rod 352 and image output facet 368 of light pipe homogenizing rod 352 to a treated skin or tissue plane 340 located between the pair of bipolar RF electrodes 328. As illustrated above (FIG. 4) image 404 of oval output facet 368 of light pipe homogenizing rod 352 could be of round or circular shape at the tissue treatment plane 340.

The laser energy could be in the infrared part of the spectrum. An LED 358 could be mounted on body 304 to illuminate the tissue or skin treatment plane 340 and facilitate the skin treatment plane observation.

Figure 5:
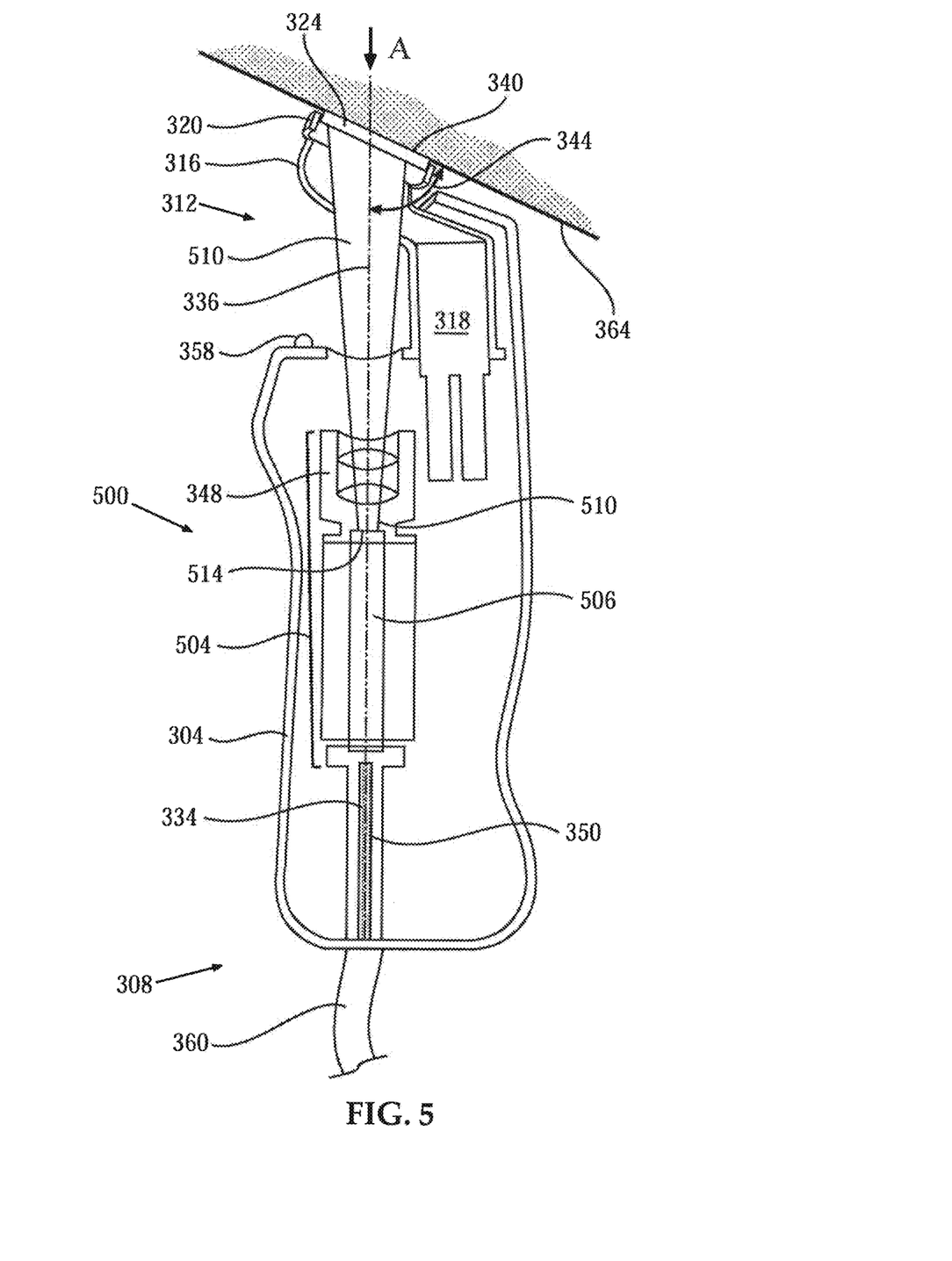
FIG. 5 is a simplified illustration of an example of optical system of an applicator configured to form a square spot in the tissue or skin treatment plane.

In another example, illustrated in FIG. 5, optical system 504 of applicator 500 includes a light homogenizing optical trapezoidal prism 506 configured to receive beam of optical energy 334 from the source of optical energy and convey or funnel the beam of optical energy 334 towards an output facet 514 that is trapezoidal in cross-section. The light pipe homogenizing rod 506 could be such as a trapezoidal prism, multi-faceted prism or a hollow light guide with a reflective coating deposited on the inner surfaces of the light guide. The output facet 514 of the trapezoidal prism 506 has a trapezoidal shape in order to form a rectangular or if desired square beam at the tissue treatment plane 340 when the applicator's axis of symmetry 336 is tilted relative to the tissue treatment plane 340.

In one example the trapezoidal or the multi-faceted rods or prisms could be tapered prisms. Tapered homogenizing rods also allow the use of shorter rods to homogenize the light energy at the treatment plane 340.

Optical system 504 further includes a pair of lenses 348 configured to receive a homogenized beam of optical energy 510 from beam homogenizing element such as for example, trapezoidal prism 506 and project the image of the output facet 514 of trapezoidal prism 506 to a treated skin or tissue area 340 located in the tissue or skin treatment plane 340. The pair of lenses can be tilted 6 to 10 degrees relative to the applicator axis to further improve homogenization of the beam at the tissue treatment plane.

Figure 5A:
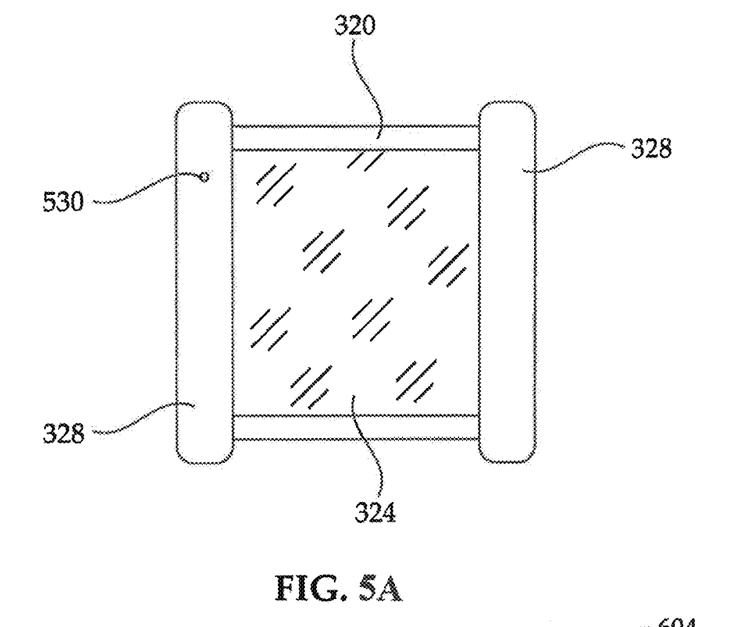
FIG. 5A is a view taken along the arrow A in FIG. 5.

As illustrated in FIG. 5A, a pair of bipolar RF electrodes 328 could be mounted on support structure 316 located on distal end 312 of housing 304. Electrodes 328 could be configured to apply RF energy to tissue located in tissue treatment plane 340. Electrodes 328 (FIG. 3A) could be mounted on frame 320. A temperature sensor 530 could be mounted on one or both electrodes 328. Temperature sensor 530 could be a thermocouple, a thermistor or other temperature sensing element.

Figure 6:
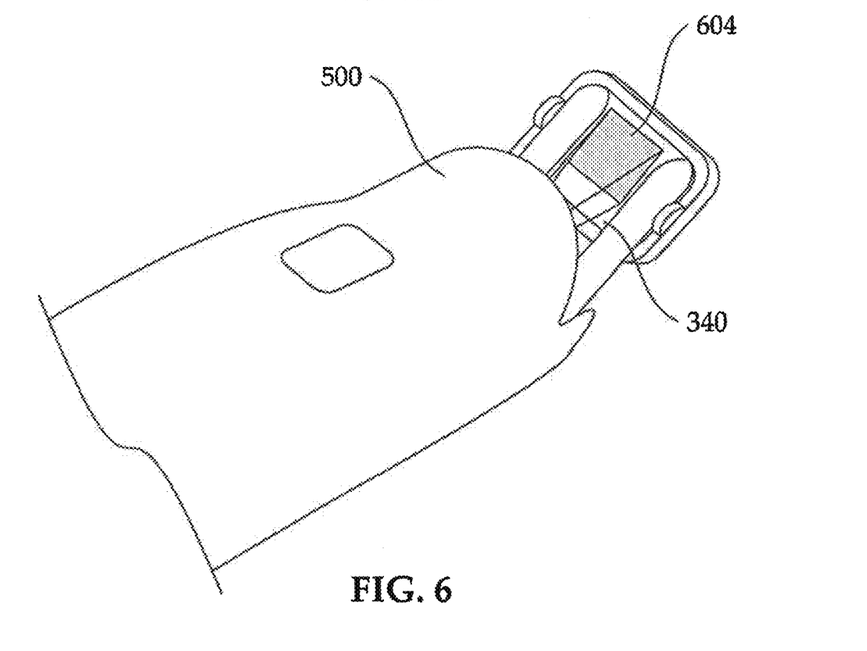
FIG. 6 is an example of a rectangular image or spot formed by optical system of the applicator of FIG. 4 in the tissue or skin treatment plane.

Image 604 (FIG. 6) of output facet 514 of trapezoidal prism that could be a tapered prism 506 has a rectangular shape. The optical energy across image or spot 604 is homogenized. When applicator 500 is moved from one treatment location to another treatment location, the rectangular image or spot 604 could be densely packed in the tissue or skin 364. Since some of the treatment could be performed by wavelengths that are not visible, applicator 500 could include a LED 358 illuminating the located between RF electrodes tissue or skin treatment area 340.

In one example, electrodes 328 are solid metal parts that could be mounted on frame 320 or support structure 316. In another example, as shown in FIG. 5A, electrodes 328 could be mounted on frame 320 or deposited on removable window 324. In one example, temperature sensors 510 configured to monitor temperature of skin treatment plane 340, could be mounted within electrodes 328. Support structure 316 is angled to applicator 300 axis of symmetry 336 or off normal relative to axis of symmetry 336 of applicator 500 and further improve line of sight to the skin treatment plane or skin area to be treated 340. The angle 344 at which support structure 316 with a pair of bipolar RF electrodes 328 is angled could be 10 to 30 degrees and usually the angle could be about 15 degrees. As shown in FIGS. 3, 4, 5 and 6 the angled support structure 316 facilitates good observation conditions of the tissue or skin treatment plane 340. (It is also possible to define the angle at which the support structure 316 is angled with respect to tissue treatment plane. Such angle would be 60 to 80 degrees.)

Support structure 316 can also be design such that it approaches the tissue treatment plane 340 from the top or bottom of the applicator (300, 500) to avoid getting in the way of the user's direct line of site of the tissue treatment plane 340. Support structure 316 can also be designed such that it has an opening or void to avoid getting in the way of the users direct line of site of the tissue treatment plane 340.

Image 604 (FIG. 6) of output facet 514 of light guide 506 has a rectangular shape at the tissue treatment plane 340. The observation of skin or tissue area being treated could be especially important when treating vascular lesions where the operator desires to see the vessel response to the treatment in real time. The optical energy across image or spot 604 (FIG. 6) is homogenized. When applicator 500 is moved from one treatment location to another treatment location, the rectangular image or spot 604 could be densely packed on the tissue or skin 364 treatment plane 340. Since some of the treatment could be performed by wavelengths that are not visible, applicator 300 could include a LED 358 with wavelength in the visible illuminating the tissue located between RF electrodes tissue or skin treatment area.

As noted above, most of the existing cosmetic light or laser based treatments are performed with a round non-homogenized light spot. Applicator 300 facilitates imaging with a round spot with homogenized optical energy distribution and imaging of a rectangular spot with homogenized optical energy distribution further improves the skin treatment and supports a good view or observation conditions of the skin or tissue plane.

Angled with respect to applicator axis of symmetry 336, which could also be an optical axis of optical systems 330 and 504, frame 316 with electrodes 328 and removable window 324 (FIG. 3) could introduce distortion in both the round 404 and rectangular spot 604. In order to compensate for this, the pair of lenses 348 could be placed at an angle to axis 336 of applicator 300 or 500. The angle could be selected to at least partially compensate for distortion of spots 404 and 604. The angle could be between 6 and 10 degrees. Good practical results have been achieved using an angle of 8 (eight) degrees.

A cable 360 extends from proximal end 308 of applicator 300 housing 304. Cable 360 connects applicator 300 to a power supply (not shown). Housing of the power supply could also incorporate a source of optical energy and a source of RF voltage. Optical fiber guide 350 could be included in cable 360. The fiber could conduct the optical energy to applicator or handpiece 300. Alternatively, an articulated arm could conduct the optical energy to handpiece 300. Although not inclusive, the source of optical energy could be a suitable laser, for example, a 595 nm pulse dye laser, a 1064 nm Nd:YAG laser, or Alexandrite 755 nm laser, or a diode laser or an assembly of diode lasers with different laser diodes emitting different light wavelengths. Selection of laser depends on the desired type of treatment.

In use applicator 500 is applied to the skin or tissue treatment plane; the source of optical energy is applied. Then, in order to treat an adjacent skin surface area the applicator is either continuously displaced over the skin or stepped from one skin segment to the other. The rectangular shape of the treatment optical energy spot does not force overlap between the stepped spots and also does not leave non-overlapped and not treated skin areas or segments.

As indicated the system could be equipped by a number of lasers to treat different skin conditions. For example, a 595 nm pulse dye laser could be used to treat different vascular conditions, Alexandrite 755 nm laser could be used for hair removal, a 1064 nm Nd:YAG laser could also be effective in treatment of different vascular conditions, different laser diodes emitting different light wavelengths could be used to treat a variety of skin condition by changing the treatment optical energy wavelength and pulse duration.

The fluence of optical energy used for skin or tissue conditions treatment could 5 to 150 J/cm2, pulse duration could be 100 psec to 1 sec, the spot size could be 10×10 mm or even 20×20 mm. Other sizes and relations between the spot size parameters could be considered including a rectangle such as 10×30 mm The authors of the current disclosure are aware that some cosmetic skin treatment system claim use of square or rectangular beams produced by a square or rectangular optical prism that is placed in contact with skin by cooling the prism. Although the latter approach has the benefit of cooling the skin surface, but in order to enhance or collect the incident light the prism is covered by light reflecting coatings and obstructs the operator's field of view.

The applicator or handpiece significantly improve observation of the tissue or skin treatment plane and facilitate the work of the operator or caregiver, providing unobstructed view of the tissue or skin treatment plane. The observation of skin or tissue area being treated could be especially important when treating vascular lesions where the operator desires to see the vessel response to the treatment in real time while keeping the applicator in place to allow further cooling immediately post treatment.

Use of the present applicator mitigates adverse effects caused by application to the skin of non-uniform distributed energies and in particular light energy.

It should be recognized that a number of variations of the above-described examples will be obvious to one of ordinary skill. Accordingly, the apparatus and method are not to be limited by those specific examples and methods as shown and described herein. Rather, the scope of the product and method is to be defined by the following claims and their equivalents.

What is claimed is:

1. An applicator, comprising:
   a pair of bipolar RF electrodes mounted on a support structure, the RF electrodes configured to contact tissue and apply RF energy to tissue located in tissue treatment plane;
   an optical system configured to receive a beam of optical energy from a source of optical energy and to project the beam of optical energy at an angle offset at least 10 degrees from normal to the tissue located in the tissue treatment plane and wherein the tissue treatment plane is located between the pair of the bipolar RF electrodes.

2. The applicator according to claim 1 wherein the optical system includes a light pipe homogenizing rod with tapered output facet configured to shape cross section of image of the tapered output facet of the light pipe homogenizing rod in the tissue treatment plane and wherein the tapered output facet of the light pipe homogenizing rod is spaced from the tissue treatment plane.

3. The applicator according to claim 2 wherein the light pipe homogenizing rod a tapered optical trapezoidal prism.

4. The applicator according to claim 1 wherein the optical system includes a pair of lenses configured to receive a homogenized beam of optical energy from light pipe homogenizing rod and image output facet of light pipe homogenizing rod to a treated skin or tissue plane located between the pair of bipolar RF electrodes and wherein the output facet of light guide has an oval shape.

5. The applicator according to claim 1 wherein the optical system includes a pair of lenses configured to receive a homogenized beam of optical energy from light pipe homogenizing rod and image output facet of light pipe homogenizing rod to a treated skin or tissue plane located between the pair of bipolar RF electrodes and wherein the image of the output facet of light pipe homogenizing rod has a trapezoidal shape.

6. The applicator according to claim 1 wherein the support structure is angled with respect to an axis of symmetry of the applicator at an angle of 10 to 30 degrees.

7. The applicator according to claim 6 wherein a pair of lenses is placed at an angle of 6 to 10 degrees to axis of the applicator.

8. The applicator according to claim 1 wherein the support structure is angled with respect axis of symmetry of the applicator and is configured to improve line of sight to the skin treatment plane or skin area to facilitate to an operator a good view of the treated tissue area.

9. The applicator according to claim 1 wherein the support structure includes a frame with a replaceable window and wherein the window is a sapphire window.

10. The applicator according to claim 9 further comprising a cooling module and wherein the cooling module is a thermoelectric element and wherein the thermoelectric element of the cooling module is configured to cool the support structure, the frame and the a sapphire window.

11. The applicator according to claim 9 further comprising a cryogenic cooling module configured to spray liquid drops of cryogen onto a surface of the tissue treatment plane when the frame is free of a window.

12. The applicator according to claim 1 wherein the source of optical energy is at least one of a group of solid state optical energy sources consisting of a 1064 nm Nd:YAG laser, or Alexandrite 755 nm laser, a diode laser or an assembly of diode lasers with different laser diodes emitting different light wavelengths.

13. The applicator according to claim 1 wherein the pair of bipolar RF electrodes is one of a group of electrodes consisting of solid metal electrode and electrodes deposited on a sapphire window.

14. The applicator according to claim 1, wherein the support structure includes at least an opening supporting easy observation of the tissue treatment plane.

15. An applicator for treating tissue comprising:
   a housing with a proximal and a distal end configured to be in contact with a segment of tissue located in a tissue treatment plane;
   a connection to a source of optical energy configured to generate a beam of optical energy;
   a light homogenizing optical prism configured to receive the beam of optical energy and wherein output facet of the light homogenizing optical prism is configured to shape and homogenize the beam of optical energy; and
   imaging optics configured to project the beam of optical energy into an optical energy spot located in the tissue treatment plane,
   wherein the imaging optics is located between the output facet of the light pipe homogenizing optical prism and the tissue treatment plane,
   wherein the applicator further comprises at least a pair of bipolar RF electrodes mounted at angle offset by at least 10 degrees from normal to the optical axis of the applicator on a frame attached to the distal end of the housing, the bipolar RF electrodes configured to be in contact with the segment of tissue located in the tissue treatment plane.

16. The applicator according to claim 15 wherein the optical energy spot located in the tissue treatment plane is located between a pair of bipolar RF electrodes.

17. The applicator according to claim 15 further comprising a cooling module and wherein the cooling module is a thermoelectric element.

18. The applicator according to claim 15 further comprising a cooling module and wherein the cooling module is a cryogenic cooling module configured to spray liquid drops of cryogen onto surface of the tissue located in the tissue treatment plane.

19. The applicator according to claim 15 wherein the distal end of the housing is angled and shaped as a support structure and wherein the support structure includes an opening facilitating real time treated skin segment observation.

20. The applicator according to claim 19 wherein the support structure includes a frame and wherein the frame includes an opening being at least one of a group of openings consisting of round and square shape opening and wherein the opening in the frame is one of a group of openings consisting of an opening including an optical element and an opening free of optical elements.

21. The applicator according to claim 20, wherein support structure and frame are in thermal communication with a cooling module.

22. The applicator according to claim 15 further comprising imaging optics and wherein the imaging optics is configured to image an output facet of the light homogenizing optical prism onto an optical energy spot in the tissue treatment plane and wherein the optical energy spot is a rectangular shaped spot.

23. The applicator according to claim 15 wherein the homogenizer prism is tapered such that the input facet of the prism is larger than the output facet.

* * * * *